United States Patent
Schurzig

(10) Patent No.: US 10,244,336 B2
(45) Date of Patent: Mar. 26, 2019

(54) S-SHAPED COUPLING SPRING FOR MIDDLE EAR IMPLANTS

(71) Applicant: MED-EL Elektromedizinische Geraete GmbH, Innsbruck (AT)

(72) Inventor: Daniel Schurzig, Hannover (DE)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 147 days.

(21) Appl. No.: 15/471,046

(22) Filed: Mar. 28, 2017

(65) Prior Publication Data
US 2017/0281942 A1    Oct. 5, 2017

Related U.S. Application Data

(60) Provisional application No. 62/314,429, filed on Mar. 29, 2016.

(51) Int. Cl.
*H04R 25/00* (2006.01)
*A61N 1/36* (2006.01)

(52) U.S. Cl.
CPC ....... *H04R 25/606* (2013.01); *A61N 1/36036* (2017.08); *H04R 25/305* (2013.01); *H04R 25/65* (2013.01)

(58) Field of Classification Search
CPC ....... H04R 25/606; H04R 25/00–25/75; H04R 2225/00–2225/83; H04R 2460/00–2460/17
See application file for complete search history.

(56) References Cited

U.S. PATENT DOCUMENTS

| 6,139,488 A | 10/2000 | Ball |
| 6,315,710 B1 | 11/2001 | Bushek et al. |
| 2014/0056453 A1 | 2/2014 | Olsen et al. |

OTHER PUBLICATIONS

International Searching Authority, International Search Report—International Application No. PCT/US2017/024430, dated May 31, 2017, together with the Written Opinion of the International Searching Authority, 13 pages.

*Primary Examiner* — Thaddeus B Cox
(74) *Attorney, Agent, or Firm* — Sunstein Kann Murphy & Timbers LLP

(57) ABSTRACT

A loading spring has an inner end that engages the outer end of a middle ear transducer, an outer end that engages a fixed anatomical structure within the middle ear of the recipient patient, and a center of mass located on a common line between the inner end and the outer end. The loading spring also has an s-shape with a central spring axis along the common line. And the loading spring is configured for displacement of the inner end and the outer end along the central spring axis to fit the loading spring between the transducer and the fixed anatomical structure with a loading force that is within a defined range and entirely along a center axis of the middle ear transducer and the central spring axis.

16 Claims, 5 Drawing Sheets

S-SHAPED COUPLING SPRING FOR MIDDLE EAR IMPLANTS

This application claims priority from U.S. Provisional Patent Application 62/314,429, filed Mar. 29, 2016, which is incorporated herein by reference in its entirety.

TECHNICAL FIELD

The present invention relates to medical implants, more specifically to a novel coupling device for a middle ear prosthesis system.

BACKGROUND ART

A normal ear transmits sounds as shown in FIG. 1 through the outer ear 101 to the tympanic membrane (eardrum) 102, which moves the ossicles of the middle ear 103 (malleus, incus, and stapes) that vibrate the oval window and round window openings of the cochlea 104. The cochlea 104 is a long narrow organ wound spirally about its axis for approximately two and a half turns. It includes an upper channel known as the scala vestibuli and a lower channel known as the scala tympani, which are connected by the cochlear duct. The cochlea 104 forms an upright spiraling cone with a center called the modiolar where the spiral ganglion cells of the acoustic nerve 113 reside. In response to received sounds transmitted by the middle ear 103, the fluid-filled cochlea 104 functions as a transducer to generate electric pulses which are transmitted to the cochlear nerve 113, and ultimately to the brain.

Hearing is impaired when there are problems in the ear's ability to transduce external sounds into meaningful action potentials along the neural substrate of the cochlea 104. To improve impaired hearing, various types of hearing prostheses have been developed. For example, when a hearing impairment is related to the operation of the middle ear 103, a conventional hearing aid or a middle ear implant (MEI) device may be used to provide acoustic-mechanical vibration to the auditory system.

FIG. 1 also shows some components in a typical MEI arrangement where an external audio processor 111 processes ambient sounds to produce an implant communications signal that is transmitted through the skin by an external transmitter 107 to an implanted receiver 108. The receiver 108 includes a receiver coil that transcutaneously receives the implant communications signal which is then demodulated into transducer stimulation signals which are sent by leads 109 through a surgically created channel in the temporal bone to a floating mass transducer (FMT) 110 secured to the incus bone in the middle ear 103. The transducer stimulation signals cause drive coils within the FMT 110 to generate varying magnetic fields which in turn vibrate a magnetic mass suspended within the FMT 110. The vibration of the inertial mass of the magnet within the FMT 110 creates vibration of the housing of the FMT 110 relative to the magnet. This vibration of the FMT 110 is typically coupled to the incus in the middle ear 103 and then to the cochlea 104 and is perceived by the user as sound. See U.S. Pat. No. 6,190,305, which is incorporated herein by reference.

Alternatively, an engagement member of the FMT 110 can be pushed against the round window membrane of the cochlear outer surface as shown in FIG. 2. The FMT 110 has an inner end 203 and an outer end 204 that are connected by a center axis 207. A conical cochlear engagement member 202 is located at the inner end 203 of the FMT 110 with a cochlear engagement surface that couples the mechanical stimulation signal to the round window membrane 201 in the outer cochlear surface. The FMT 110 is pressed against the round window membrane 201 by a fascia piece 205 made of cartilage that is filled into the space between the FMT 110 and the temporal bone 206 of the middle ear which acts as a fixing anatomical structure. The fascia piece 205 is biocompatible and possesses suitable damping properties for stabilizing the FMT 110 in place against the round window membrane 201 and to prevent it from wandering out of place. But this approach depends very much on the exact execution of the filling of the fascia piece 205, which is manually cut to size by the surgeon and yields non-reproducible results. In addition, exerting too much or too little pressure on the round window membrane 201 can yield a distorted sound percept by the patient. Preliminary studies have shown that the preload force on the FMT 110 should lie between 10 and 20 mN to optimally couple the FMT 110 to the round window membrane 201.

U.S. Pat. No. 9,191,760 shows a loading spring 302 in the form of an eccentric spring device, but in that arrangement, the center of gravity 304 of the loading spring 302 does not lie on the center axis 303 of the FMT 110 and the round window engagement member 301. Furthermore, the structural composition of the spring element results in a loading force 305 which is not collinear with the excitation force of the FMT, i.e. the central axis 303 of the FMT 110. Due to these two spring properties, the active FMT 110 will not only move back and forth along its central axis 303, but will also show a rotational component 306 that is offline from the center axis 303. This decreases the vibrational energy introduced into the auditory system by the vibrational oscillations.

SUMMARY OF THE INVENTION

Embodiments of the present invention are directed to a middle ear implant arrangement with an implantable electromechanical transducer that has an inner end and an outer end, which are connected by a center transducer axis. A cochlear engagement member is located at the inner end of the transducer with a cochlear engagement surface that couples a mechanical stimulation signal to an outer cochlear surface of a recipient patient. A loading spring has an inner end that engages the outer end of the transducer, an outer end that engages a fixed anatomical structure within the middle ear of the recipient patient, and a center of mass located on a common line between the inner end and the outer end. The loading spring has an s-shape with a central spring axis along this common line. The loading spring is designed such that inner and outer ends are to be displaced along the central spring axis to create a loading force within a defined range. The exact value of the force depends on the distance between the transducer and the fixed anatomical structure on the back end. Any displacement within this range will keep the generated loading force collinear with the central axis of the transducer.

In further specific embodiments, the loading spring has an s-shape that lies in a two-dimensional plane. And the loading spring may be point symmetric about the spring's center of mass. The loading spring may be configured for displacement of the inner end and the outer end of up to 200 μm with a loading force that is within the defined range; for example, a loading force is up to 100 mN, preferably 10-20 mN. And the loading spring may be made of Nitinol or titanium.

DETAILED DESCRIPTION OF SPECIFIC EMBODIMENTS

Figure 1:
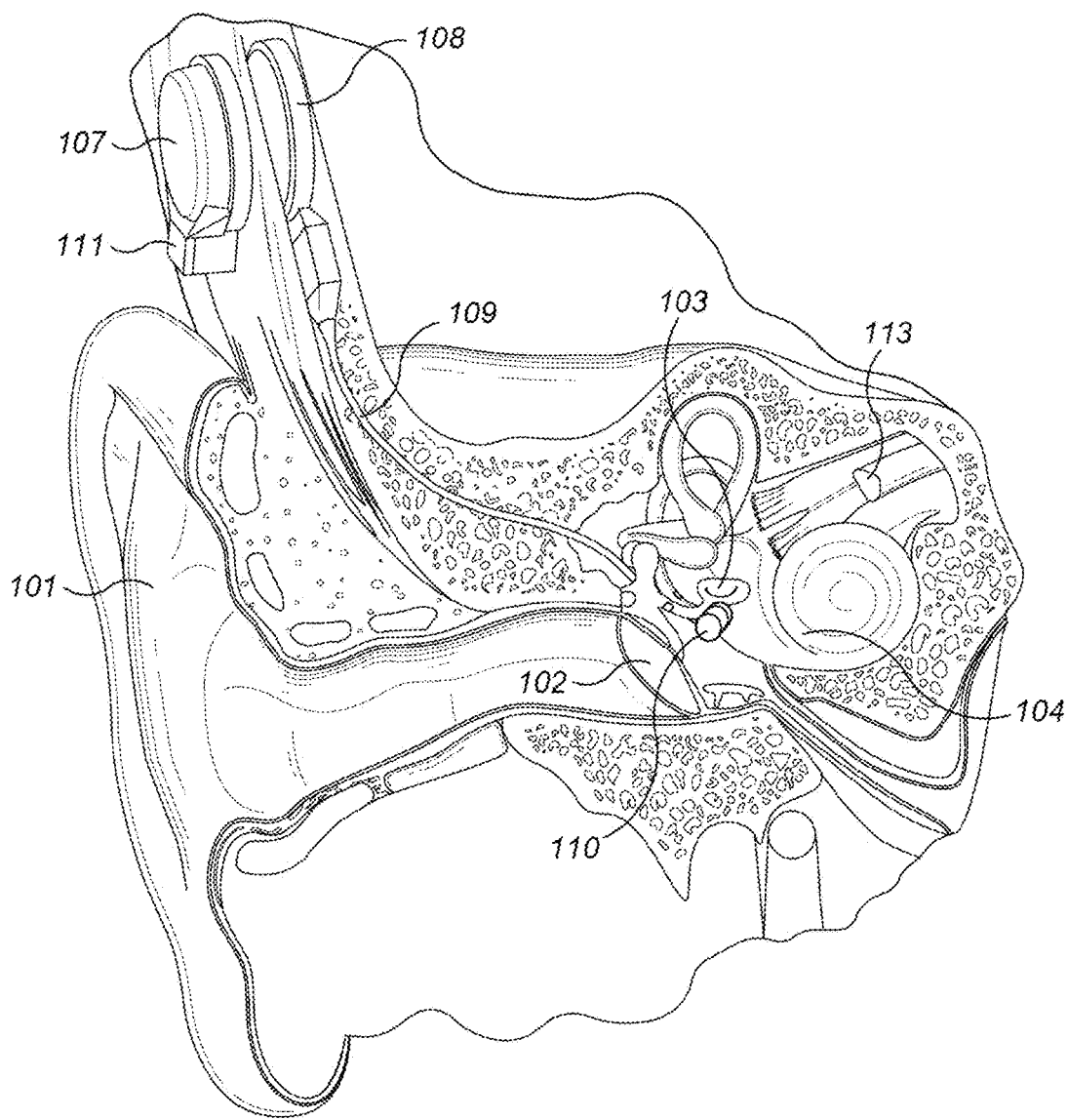
FIG. 1 shows various anatomical structures of a normal human ear with a middle ear implant using a floating mass transducer.
Figure 2:
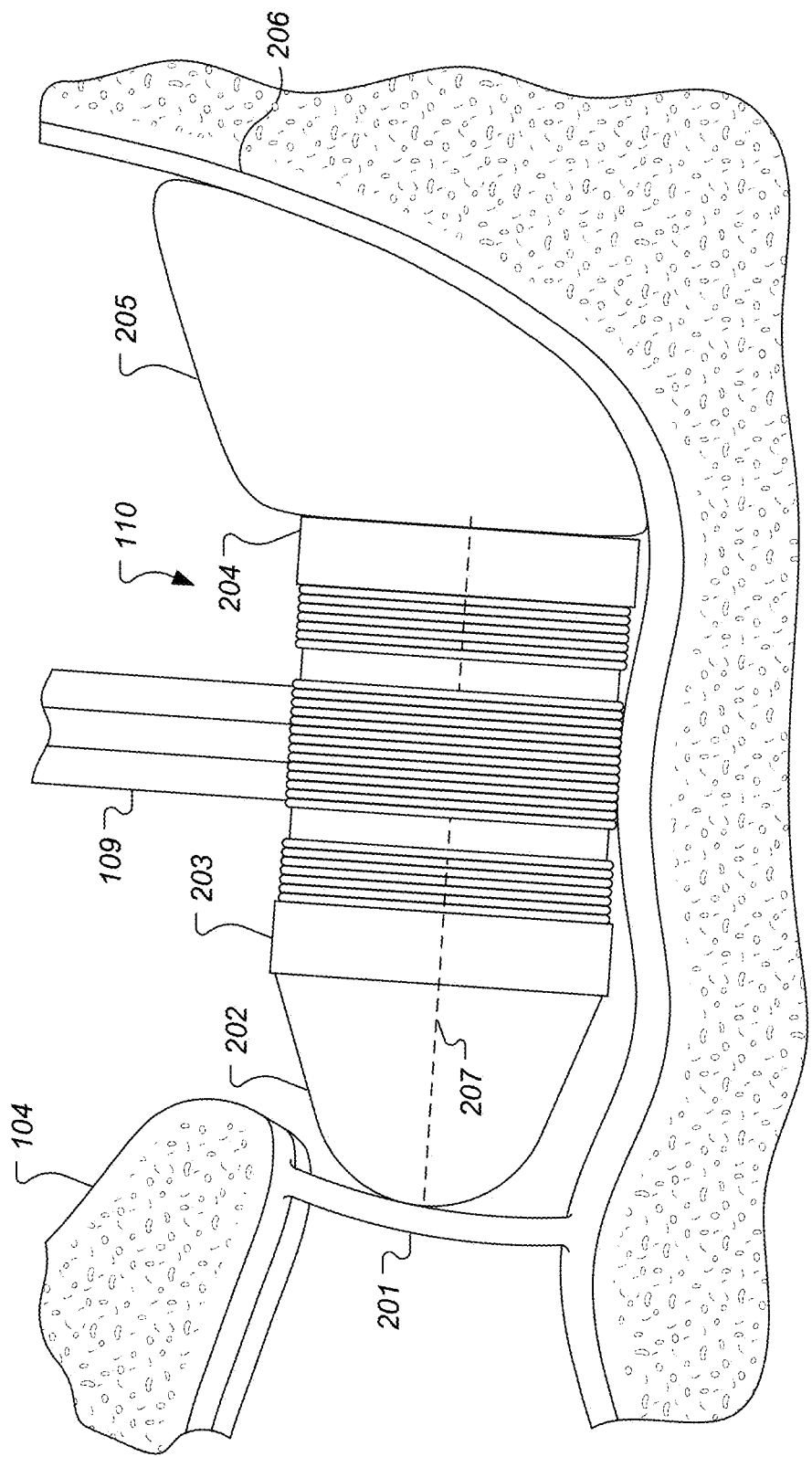
FIG. 2 shows details of coupling a middle ear transducer to a round window membrane according to the prior art.
Figure 3:
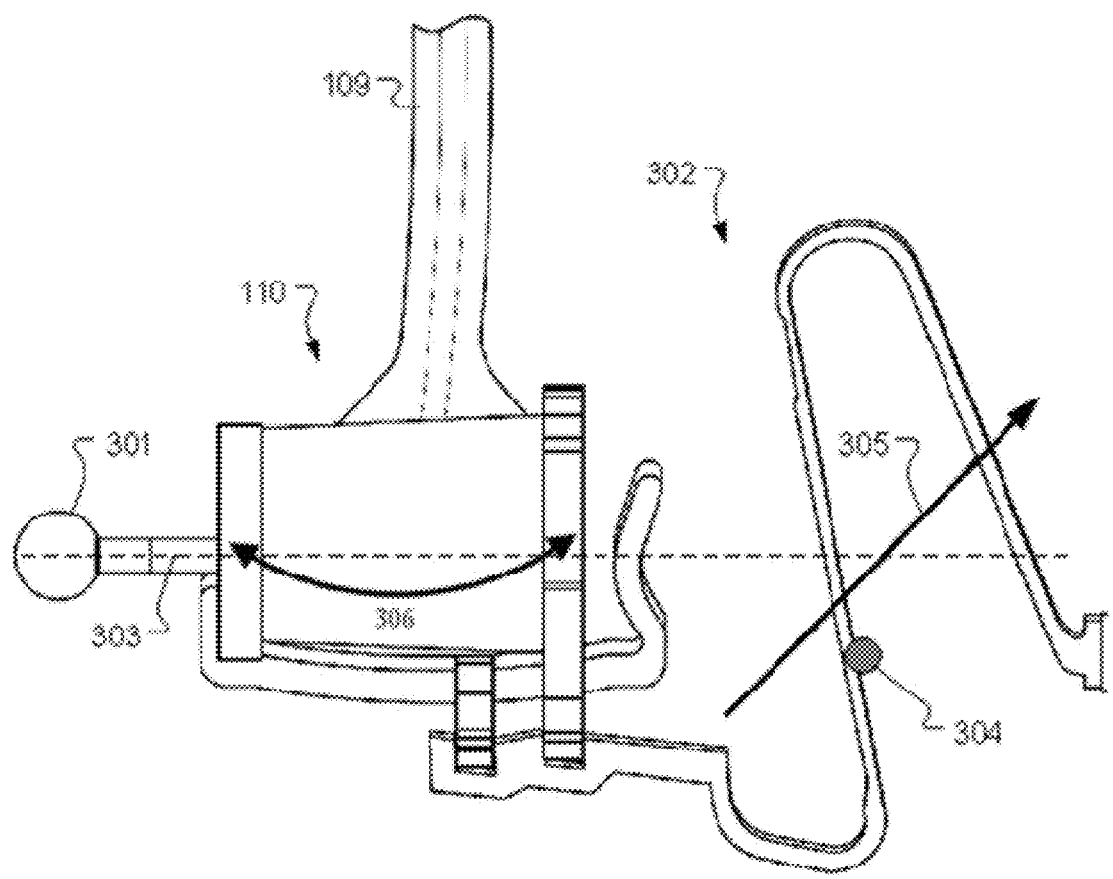
FIG. 3 shows an example of a loading spring according to the prior art.

Various embodiments of the present invention are directed to a middle ear implant arrangement based on an improved loading spring for a middle ear transducer. The spring is adapted to develop a loading force that presses against one end of the electromechanical transducer to firmly engage it against an outer surface of the patient's cochlea (e.g. the round window) with a force that is within a defined range and entirely along the center axis of the transducer, which is also a central axis of the loading spring. For example, the middle ear transducer may be an FMT 110 as shown in FIGS. 1 and 2 with an inner end 203 and an outer end 204. The ends are connected by a center axis 207, and with a conical cochlear engagement member 202 at the inner end 203 with a cochlear engagement surface that couples the mechanical stimulation signal to the round window membrane 201 in the outer cochlear surface.

Figure 4:
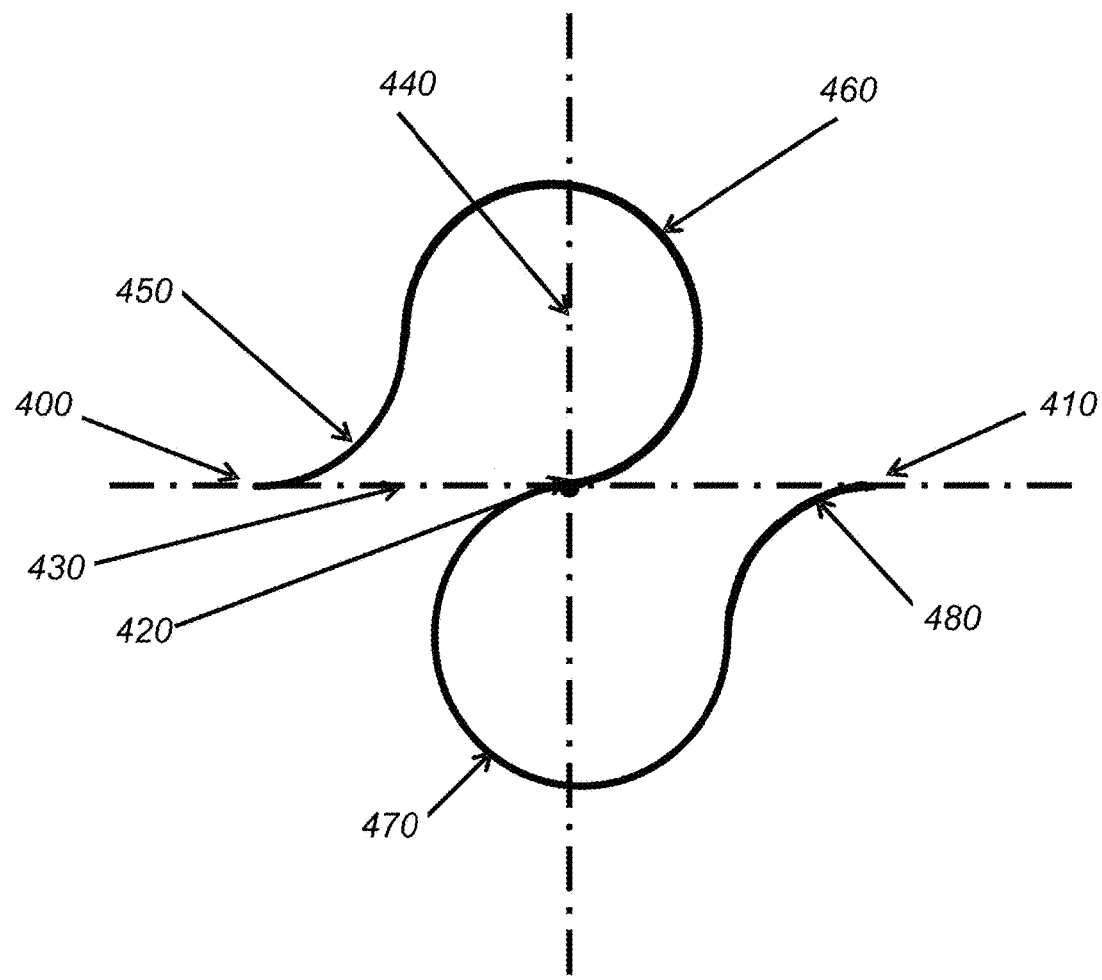
FIG. 4 shows a side view of a loading spring according to an embodiment of the present invention.

FIG. 4 shows one specific embodiment where a loading spring has an inner end 400 that engages the outer end of the transducer, an outer end 410 that engages a fixed anatomical structure within the middle ear of the recipient patient, and a center of mass 420 located on a common line between the inner end 400 and the outer end 410. The loading spring has an s-shape that lies entirely in a two-dimensional plane with a central axis 430 along the common line. The loading spring also is configured for displacement of the inner end 400 and the outer end 410 along the central spring axis 430 so as to fit the loading spring between the transducer and the fixed anatomical structure with a loading force that is within a defined range and entirely along the center axis of the transducer and the central spring axis 430. Preferably, this relation is maintained over as long of a displacement range as possible up to 200 µm and more while delivering the desired loading force range; for example, a loading force of 10-20 mN.

The s-shape of the loading spring also has a symmetry point at the center of mass 420. Applying a loading force of up to about 100 mN along the central spring axis 430 substantially maintains the point symmetry, and the absolute value of the curvature along the s-shape is constant. The point symmetry characteristic keeps the center of mass 420 located on the central spring axis 430. The first derivative of the S-shape at the inner end 400 and the outer end 410 is (nearly) zero. The center of mass 420 is an inflection point in the s-shape with a second derivative at or near zero, which also is maintained when applying a loading force of up to about 100 mN along the central spring axis 430. More specifically, if the curvature of a first spring section 450 is denoted by some specific value a, the curvature of a second spring section 460 is −a, the curvature of a third spring section 470 is again a, and the curvature of a fourth spring section 480 is again −a. In other words, the loading spring is comprised of a plurality of spring sections having the same absolute values of curvatures.

As previously discussed, a loading force of 10-20 mN may be optimal, however, any loading force of up to about 100 mN can be applied since the loading spring undergoes uniform deformation over the entire S-shape. The relations between the specific curvatures of the different spring sections may vary by up to about 10%. In particular the relation of the curvatures of all the spring sections of the loading spring is maintained. As a result, no one particular portion of the spring element is more prone to breakage than any other one, and so there is no need to introduce different diameter sections.

The overall spring stiffness can be selected such that a displacement of up to 200 µm or even more can be achieved while ensuring the desired loading force of 10-20 mN. The actual relation of the displacement and loading force also depends on the thickness of the spring. The overall height of the loading spring may be comparable to the diameter of the cylindrical transducer housing; e.g., about 1.5 mm. This is a convenient feature for manufacturing such a device. The specific values as to applicable loading forces and displacements depend on the actual slope of the loading spring around the symmetry point as well as the thickness/diameter of the material used, which may be any biocompatible material such as Nitinol or titanium.

Figure 5:
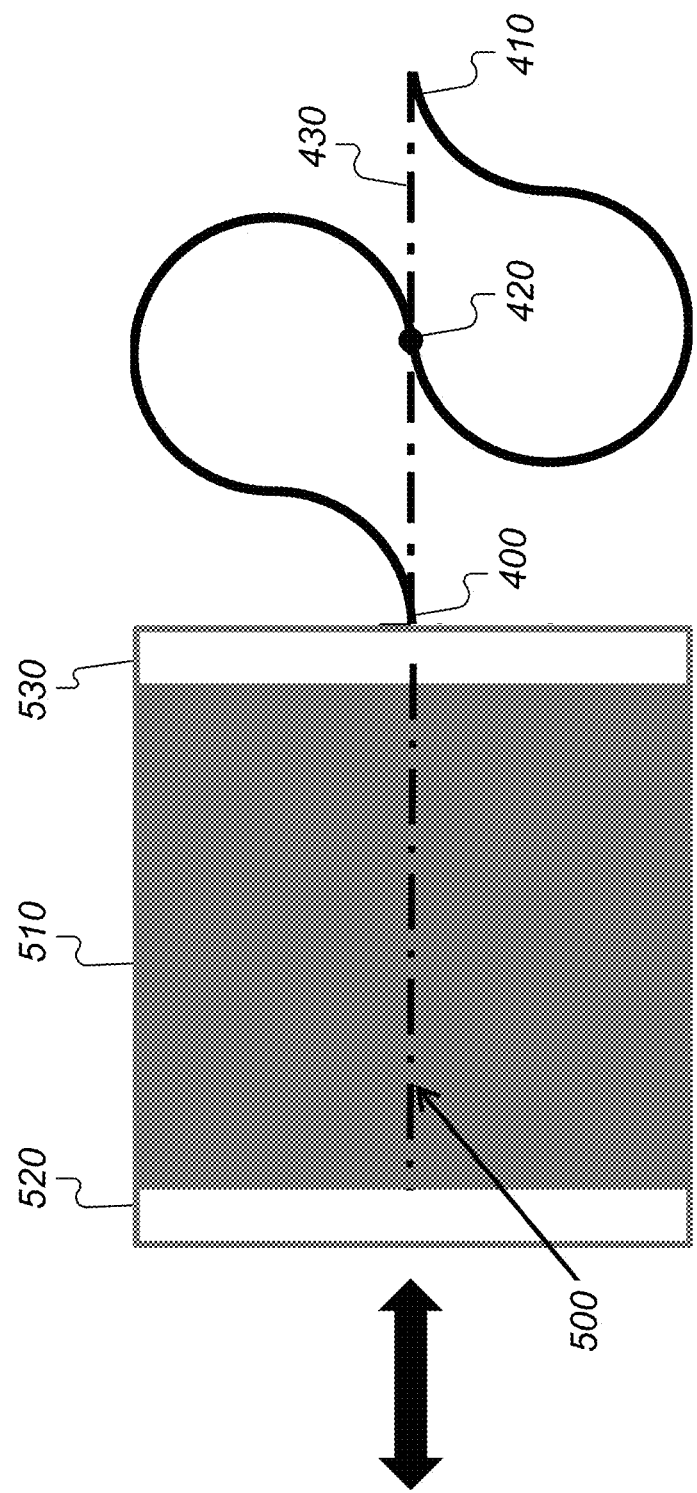
FIG. 5 shows a side view of a loading spring as in FIG. 4 engaged against a middle ear transducer.

FIG. 5 shows a side view of a loading spring as in FIG. 4 which is engaged against a middle ear transducer 510, which has an outer end 530 coupled to the loading device and an inner end 520 directed towards the round window membrane. The inner end 400 of the loading spring is attached (directly or e.g. by means of a coupler element—not shown in the figures) to the outer end 530 of the transducer 510 so that the driving force of the created vibrations acts along the central spring axis 430 and through the center of mass 420 of the loading spring. So if an FMT specifically is used as the transducer 510, then the inner end 400 of the loading spring is attached to the center axis 500 of the cylindrically shaped FMT (which also has a uniform mass distribution around its central axis). At any phase during oscillation of the FMT transducer 510 against the round window membrane, the applied force is along the central spring axis 430 and there is no rotational force component off angle from the axis. So no torque is applied to the transducer 510 or any middle ear anatomical structure because of the alignment of central spring axis 430 and center transducer axis 500.

Although various exemplary embodiments of the invention have been disclosed, it should be apparent to those skilled in the art that various changes and modifications can be made which will achieve some of the advantages of the invention without departing from the true scope of the invention.

What is claimed is:

1. A middle ear implant arrangement comprising:
    an implantable electromechanical transducer with an inner end and an outer end connected by a center transducer axis, configured to convert an input electrical stimulation signal into a corresponding output mechanical stimulation signal;
    a cochlear engagement member located at the inner end of the transducer with a cochlear engagement surface configured to couple the mechanical stimulation signal to an outer cochlear surface of a recipient patient; and
    a loading spring having:

i. an inner end that engages the outer end of the transducer, ii. an outer end configured to engage a fixed anatomical structure within a middle ear of the recipient patient; and iii. a center of mass located on a common line between the inner end and the outer end of the loading spring;

wherein the loading spring has an s-shape with a central spring axis along the common line, and wherein the loading spring is configured for displacement of the inner end and the outer end of the loading spring along the central spring axis so as to fit the loading spring between the transducer and the fixed anatomical structure with a loading force that is within a defined range and entirely along the center transducer axis and the central spring axis.

2. The middle ear implant arrangement according to claim 1, wherein the loading spring has an s-shape lying in a two-dimensional plane.

3. The middle ear implant arrangement according to claim 1, wherein the loading spring is point symmetric about the center of mass.

4. The middle ear implant arrangement according to claim 1, wherein the loading spring is configured for displacement of the inner end and the outer end of the loading spring of up to 200 μm with a loading force that is within the defined range.

5. The middle ear implant arrangement according to claim 1, wherein the loading force is up to 100 mN.

6. The middle ear implant arrangement according to claim 1, wherein the defined range is 10-20 mN.

7. The middle ear implant arrangement according to claim 1, wherein the loading spring is made of Nitinol or titanium.

8. The middle ear implant arrangement according to claim 1, wherein the loading spring comprises of a plurality of spring sections having equal absolute values of curvatures.

9. A loading spring for a middle ear implant comprising:

an inner end configured to engage an outer end of a middle ear transducer, an outer end configured to engage a fixed anatomical structure within a middle ear of a recipient patient; and a center of mass located on a common line between the inner end and the outer end of the loading spring;

wherein the loading spring has an s-shape with a central spring axis along the common line, and wherein the loading spring is configured for displacement of the inner end and the outer end of the loading spring along the central spring axis so as to fit the loading spring between the transducer and the fixed anatomical structure with a loading force that is within a defined range and entirely along a center axis of the middle ear transducer and the central spring axis.

10. The loading spring according to claim 9, wherein the loading spring has an s-shape lying in a two-dimensional plane.

11. The loading spring according to claim 9, wherein the loading spring is point symmetric about the center of mass.

12. The loading spring according to claim 9, wherein the loading spring is configured for displacement of the inner end and the outer end of the loading spring of up to 200 μm with a loading force that is within the defined range.

13. The loading spring according to claim 9, wherein the loading force is up to 100 mN.

14. The loading spring according to claim 9, wherein the defined range is 10-20 mN.

15. The loading spring according to claim 9, wherein the loading spring is made of Nitinol or titanium.

16. The loading spring according to claim 9, wherein the loading spring comprises of a plurality of spring sections having equal absolute values of curvatures.

\* \* \* \* \*